(12) United States Patent
Deliencourt-Godefroy et al.

(10) Patent No.: US 10,744,181 B2
(45) Date of Patent: Aug. 18, 2020

(54) GLYCOPEPTIDE DERIVATIVES FOR USE IN THE TREATMENT AND/OR PREVENTION AND/OR ATTENUATION OF FIBROSIS DISEASES

(71) Applicant: TFCHEM, Val de Reuil (FR)

(72) Inventors: Géraldine Deliencourt-Godefroy, Bois d'Ennebourg (FR); Jocelyne Legoedec, Sotteville-les-Rouen (FR)

(73) Assignee: TFCHEM (FR)

( * ) Notice: Subject to any disclaimer, the term of this patent is extended or adjusted under 35 U.S.C. 154(b) by 0 days.

(21) Appl. No.: 16/482,040

(22) PCT Filed: Jan. 30, 2017

(86) PCT No.: PCT/IB2017/000207
§ 371 (c)(1),
(2) Date: Jul. 30, 2019

(87) PCT Pub. No.: WO2018/138541
PCT Pub. Date: Aug. 2, 2018

(65) Prior Publication Data
US 2019/0388501 A1  Dec. 26, 2019

(51) Int. Cl.
*A61K 38/14* (2006.01)
*A61K 31/70* (2006.01)
*A61P 17/02* (2006.01)
*A61K 9/00* (2006.01)

(52) U.S. Cl.
CPC ............ *A61K 38/14* (2013.01); *A61K 9/0014* (2013.01); *A61K 31/70* (2013.01); *A61P 17/02* (2018.01)

(58) Field of Classification Search
None
See application file for complete search history.

(56) References Cited

FOREIGN PATENT DOCUMENTS

| WO | 2006059227 A1 | 6/2006 |
| WO | 2007125203 A1 | 11/2007 |
| WO | 2007128899 A2 | 11/2007 |
| WO | 2015140178 A1 | 9/2015 |

OTHER PUBLICATIONS

Chin et al., "Differential Expression of Transforming Growth Factor-B Receptors I and II and Activation of Smad 3 in Keloid Fibroblasts", Plastic and Reconstructive Surgery, vol. 108, No. 2, Aug. 2001, pp. 423-429.
International Search Report from Application No. PCT/IB2017/000207 dated Oct. 2, 2017, pp. 1-3.
Jumper et al., "Functional histopathology of keloid disease", Journal of Histology and Histopathology, Cellular and Molecular Biology, vol. 30, Apr. 22, 2015, pp. 1033-1057.
Olczyk et al., "The Role of the Extracellular Matrix Components in Cutaneous Wound Healing", BioMed Research International, vol. 2014, Article ID 747584, Mar. 2014, pp. 1-9.
Seleit et al., "Immunohistochemical Evaluation of Leptin Expression in Wound Healing: A Clue to Exuberant Scar Formation", Appl. Immunohistochem Mol. Morphol, vol. 24, No. 4, Apr. 2016, pp. 296-306.

*Primary Examiner* — Brian J Davis
(74) *Attorney, Agent, or Firm* — Lerner, David, Littenberg, Krumholz & Mentlik, LLP

(57) ABSTRACT

The present invention relates to a compound of the following formula (I), as well as to a pharmaceutical composition comprising at least one compound of following formula (I) and at least one pharmaceutically acceptable excipient, for use in the treatment and/or prevention and/or attenuation of fibrosis diseases, in particular excessive scars such as keloids or hypertrophic scars.

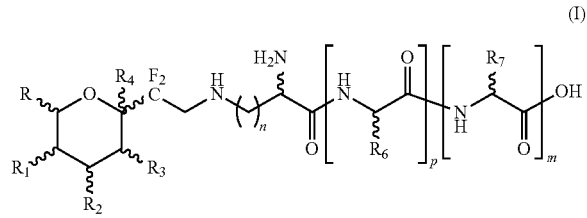

21 Claims, No Drawings

GLYCOPEPTIDE DERIVATIVES FOR USE IN THE TREATMENT AND/OR PREVENTION AND/OR ATTENUATION OF FIBROSIS DISEASES

CROSS-REFERENCE TO RELATED APPLICATIONS

The present application is a national phase entry under 35 U.S.C § 371 of International Application No. PCT/IB2017/000207 filed Jan. 30, 2017, which is hereby incorporated herein by reference.

The present invention relates to glycopeptide derivatives, as well as pharmaceutical compositions containing such compounds, for use in the treatment and/or prevention and/or attenuation of fibrosis diseases and in particular for the treatment and/or prevention and/or attenuation of excessive scars such as keloids or hypertrophic scars.

During the classical wound healing process, three main complex steps are involved: 1) hemostasis/inflammation, 2) proliferation and 3) remodeling (*BioMed Research International* 2014, article ID747584). First, the aggregation of platelets and the delivery of cytokines stop the hemorrhage and prevent infection (formation of a fibrin clot). Then, the proliferation of fibroblasts, the angiogenesis and the synthesis of extracellular matrix lead to the regeneration of dermal and epidermal tissue. And finally, the remodeling of the granulation tissue occurs.

Keloids and hypertrophic scars are the result of a dysfunction in the classical wound healing process following injury such as a surgical intervention, piercings, vaccination, acne, cuts, or burns. They consist of unaesthetic dense fibrous tissue that extends beyond the initial site of injury for the keloids or remain within the initial boundaries of injury for the hypertrophic scars.

Numerous treatments have been developed in order to treat, reduce and/or prevent keloids and hypertrophic scars such as conventional surgery, pressure therapy, topical silicone gel, radiation, laser, cryosurgery, injection of corticosteroids and chemical agents. Despite the large number of possible options to prevent and/or treat and/or attenuate keloids, none of them are really effective.

In this invention, an unexpected role of glycopeptide derivatives in the regulation of several genes involved in mechanism of reducing/treating/preventing fibrosis diseases such as keloids has been discovered.

This invention relates thus to a compound of the following formula I,

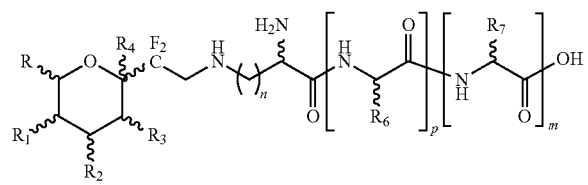

or a salt thereof, a solvate, a tautomer, a stereoisomer or a mixture of stereoisomers in any proportions, in particular a mixture of enantiomers, and particularly a racemate mixture, in which:

n represents an integer from 1 to 6,
m represents 0 or 1,
p represents 0 or 1

R represents H, F, $CH_3$, $CH_2F$, or $CH_2OH$,
$R_1$, $R_2$ and $R_3$ represent, independently from one another, H, F, or OH,
$R_4$ represents a hydrogen, a halogen, or OH,
$R_6$ and $R_7$ represent, independently from each other, a hydrogen, a ($C_1$-$C_6$)alkyl, an aryl, or an aryl-($C_1$-$C_6$) alkyl, for use in the treatment and/or prevention and/or attenuation of fibrosis diseases, in particular excessive scars such as keloids or hypertrophic scars.

The present invention relates also to the use of a compound of formula I as defined above, or a salt thereof, a solvate, a tautomer, a stereoisomer or a mixture of stereoisomers in any proportions, in particular a mixture of enantiomers, and particularly a racemate mixture, for the manufacture of a medicament intended for the treatment and/or prevention and/or attenuation of fibrosis diseases, in particular excessive scars such as keloids or hypertrophic scars.

The present invention relates also to the use of a compound of formula I as defined above, or a salt thereof, a solvate, a tautomer, a stereoisomer or a mixture of stereoisomers in any proportions, in particular a mixture of enantiomers, and particularly a racemate mixture, in the treatment and/or prevention and/or attenuation of fibrosis diseases, in particular excessive scars such as keloids or hypertrophic scars.

The present invention relates also to a method of treating and/or preventing and/or attenuating fibrosis diseases, in particular excessive scars such as keloids or hypertrophic scars, comprising the administration to a person in need thereof of an effective amount of a compound of formula I as defined above, or a salt thereof, a solvate, a tautomer, a stereoisomer or a mixture of stereoisomers in any proportions, in particular a mixture of enantiomers, and particularly a racemate mixture.

Such compounds of formula I were described in international application WO2015/140178, as well as their process of manufacture. These compounds are disclosed in this application for their use in the preservation and/or protection and/or regeneration of biological materials or microorganisms and for cosmetic applications such as anti-aging, skin protection or skin regeneration. In this application, it has been proven that the $CF_2$ glycopeptides of formula I have a significant preservative/protective effect on human skin fibroblasts and human nasal epithelial cells in vitro under different stresses as in particular starvation conditions, UV stress, oxidative stress or bacterial stress. There is no mention of potential application of these compounds for the treatment of fibrosis diseases as in particular hypertrophic scars and keloids. Moreover, such an application is not evident to a person skilled in the art.

The compounds according to the invention can be used in combination with, and more particular after, a laser or surgical treatment. Indeed, a patient suffering from a fibrosis disease, in particular excessive scars such as keloids or hypertrophic scars, can be first treated with laser or by surgery to eliminate the excess fibrous connective tissue and then a compound according to the invention can be applied topically on the wound during its healing in order to prevent the reappearance of the excess fibrous connective tissue.

In the context of the present invention, a salt can be:
(1) an acid addition salt formed with an inorganic acid such as hydrochloric, hydrobromic, sulfuric, nitric and phosphoric acid and the like; or formed with an organic acid such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L-tartaric, tartaric, p-toluenesulfonic, trimethylacetic and trifluoroacetic acid and the like, or (2) a salt formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate, sodium hydroxide and the like.

In the context of the present invention, solvates of the compounds of the present invention include conventional solvates such as those formed during the last step of the preparation of the compounds of the invention due to the presence of solvents. As an example, mention may be made of solvates due to the presence of water (these solvates are also called hydrates) or ethanol.

For the purpose of this invention, "tautomer" is intended to designate the various tautomer forms that the sugar of compound of formula (I) may assume, namely a pyranose (6-membered ring), furanose (5-membered ring) or linear (open form) form. However, for practical reasons, the sugar of compound of formula (I) is represented in the present description by its pyranose form.

However, the compounds of the invention can assume various tautomer forms only when the radical $R_4$ represents an OH group, $R_1$ having also to represent an OH group in order that the compounds of the invention can be in the furanose form.

Thus, for example, in the galactose series, the compounds of the invention might appear under the following various forms:

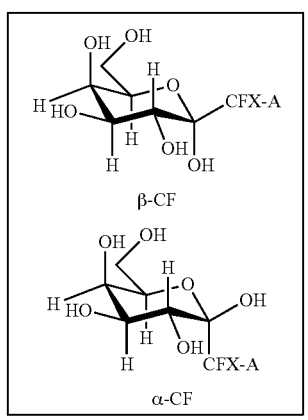

Pyranoses

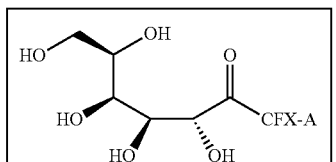

Linear

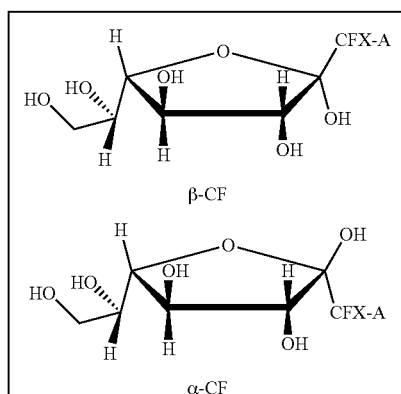

Furanoses

The group

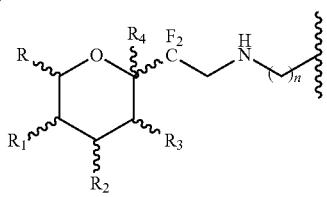

when $R_4=R_1=OH$ can thus assume the following tautomer forms:

pyranose form:

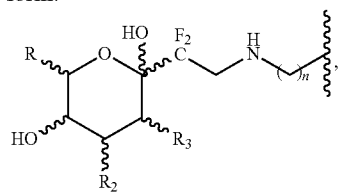

furanose form:

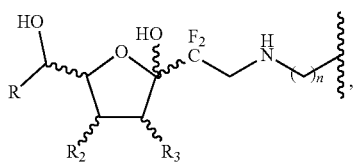

and
linear form:

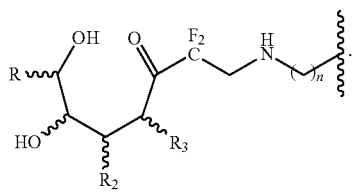

In the same way, the group

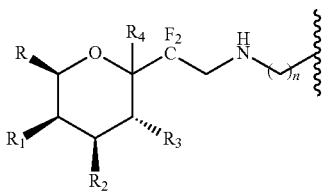

when $R_4=R_1=OH$ can thus assume the following tautomer forms:

pyranose form:

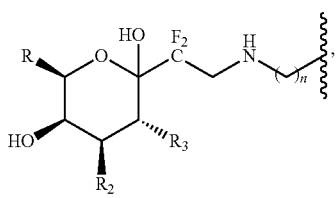

furanose form:

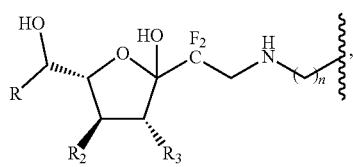

and
linear form:

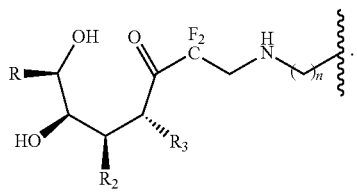

The anomeric carbon can appear in two different configurations in the closed pyranose and furanose forms.

The compounds of the invention can assume different tautomer forms which can be present in solution in equilibrium, with optionally a major tautomer form relatively to the other(s) tautomer form(s), or the compounds of the invention can assume only one tautomer form, such as only a pyranose form. This will depend notably on the nature of the medium, the temperature, the concentration of the compound, etc.

In this last case where the sugar assumes only one tautomer form, it is possible to block the configuration of the sugar in this tautomeric form when $R_4=OH$ is transformed, notably by substitution of the OH group or conversion in a hydrogen or halogen atom.

Within the meaning of this invention, "stereoisomers" is intended to designate diastereoisomers or enantiomers. These are therefore optical isomers. Stereoisomers which are not mirror images of one another are thus designated as "diastereoisomers," and stereoisomers which are non-superimposable mirror images are designated as "enantiomers".

Notably, the sugar moiety and the amino acid moieties of the compounds of the invention can belong to the D or L series.

A carbon atom bond to four non-identical substituents is called a "chiral centre".

An equimolar mixture of two enantiomers is called a racemate mixture.

The term "halogen" as used in the present invention refers to an atom of fluorine, bromine, chlorine or iodine. Advantageously, this is an atom of fluorine.

The term "$(C_1$-$C_6)$-alkyl" as used in the present invention refers to a saturated, linear or branched hydrocarbon chain comprising from 1 to 6 carbon atoms, in particular the methyl, ethyl, n-propyl, isopropyl, n-butyl, iso-butyl, sec-butyl, tert-butyl, n-pentyl, n-hexyl groups. It can be in particular a methyl group.

The term "aryl", as used in the present invention, refers to an aromatic hydrocarbon group comprising preferably 6 to 10 carbon atoms and comprising one or more fused rings, such as, for example, a phenyl or naphtyl group. Advantageously, it will be a phenyl group.

The term "aryl-$(C_1$-$C_6)$-alkyl" as used in the present invention refers to any aryl group as defined above, which is bound to the molecule by means of a $(C_1$-$C_6)$-alkyl group as defined above. In particular, it can be a benzyl group.

By "fibrosis disease" is meant in the present invention a disease involving the formation of excess fibrous connective tissue. When this formation of excess fibrous connective tissue occurs in response to injury (for ex. a surgical intervention, piercings, vaccination, acne, cuts, or burns), the fibrosis disease is called "excessive scar". It can be keloids or hypertrophic scars. They consist of unaesthetic dense fibrous tissue that extends beyond the initial site of injury for the keloids or remain within the initial boundaries of injury for the hypertrophic scars.

By "treatment" of a disease is meant in the present invention the disappearance of the symptom(s) of the disease, i.e. the excess fibrous connective tissue in the case of a fibrosis disease.

By "prevention" of a disease is meant in the present invention the fact to prevent or reduce the appearance of the symptom(s) of the disease, i.e. the excess fibrous connective tissue in the case of a fibrosis disease.

By "attenuation" of a disease is meant in the present invention the modulation, in particular the reduction of the symptom(s) of the disease, i.e. the excess fibrous connective tissue in the case of a fibrosis disease. It can be for example the reduction of the amount excess fibrous connective tissue. Thus, the size of a keloid or hypertrophic scar can be reduced.

According to a particular embodiment, the compounds of formula I of the present invention have one of the following formulas (Ia), (Ib), (Ic):

(Ia)

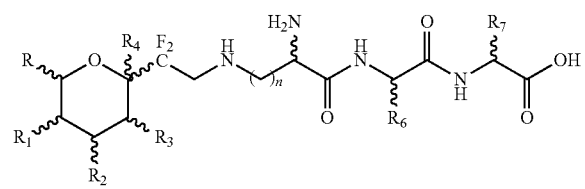

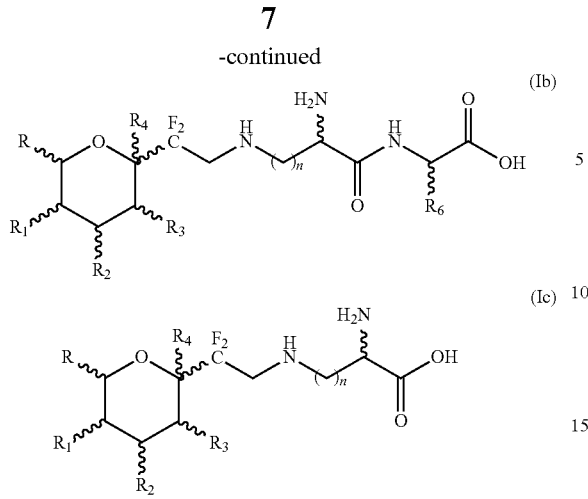

in which n, R, $R_1$, $R_2$, $R_3$, $R_4$, $R_6$ and $R_7$ are as defined above or below.

According to a particular embodiment, n represents an integer from 2 to 6, notably from 3 to 5, such as 4.

R can represent more particularly a $CH_2OH$ group.

$R_1$, $R_2$ and $R_3$ can each represent a OH group.

According to a particular embodiment, R represents a $CH_2OH$ group and $R_1$, $R_2$ and $R_3$ each represent a OH group.

$R_4$ can represent more particularly a OH group.

According to a particular embodiment, R represents a $CH_2OH$ group and $R_1$, $R_2$, $R_3$ and $R_4$ each represent a OH group.

$R_6$ and $R_7$ can represent, independently from each other, a $(C_1$-$C_6)$alkyl, an aryl or an aryl-$(C_1$-$C_6)$alkyl; more particularly a $(C_1$-$C_6)$alkyl such as a methyl.

According to a particular embodiment, R represents a $CH_2OH$ group; $R_1$, $R_2$, $R_3$ and $R_4$ each represent a OH group; and $R_6$ and $R_7$ represent, independently from each other, a $(C_1$-$C_6)$alkyl such as a methyl.

The compound of the present invention can be chosen among the following compounds:

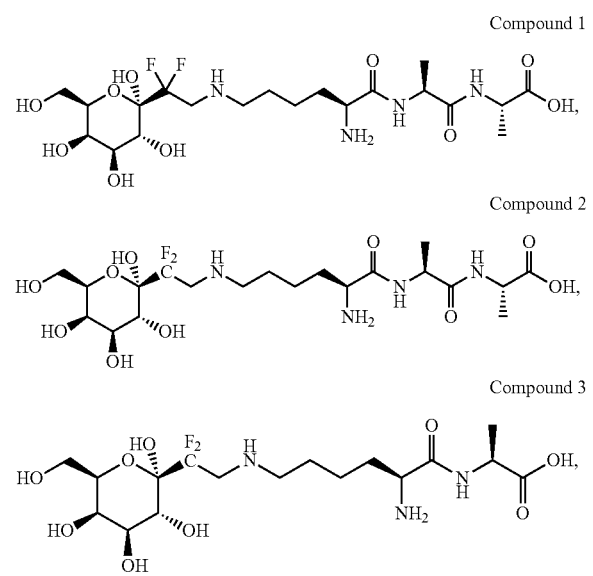

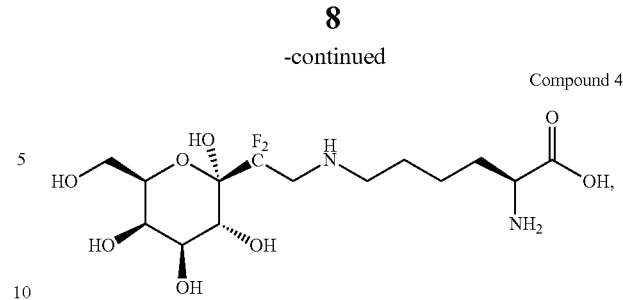

and salts and/or solvates thereof.

The present invention relates also to a pharmaceutical composition comprising at least one compound of formula I as defined above, according to any of the disclosed embodiments, or a salt thereof, a solvate, a tautomer, a stereoisomer or a mixture of stereoisomers in any proportions, in particular a mixture of enantiomers, and particularly a racemate mixture, and at least one pharmaceutically acceptable excipient, for use in the treatment and/or prevention and/or attenuation of fibrosis diseases, in particular excessive scars such as keloids or hypertrophic scars.

The present invention relates also to the use of said pharmaceutical composition for the manufacture of a medicament intended for the treatment and/or prevention and/or attenuation of fibrosis diseases, in particular excessive scars such as keloids or hypertrophic scars.

The present invention relates also to the use of said pharmaceutical composition in the treatment and/or prevention and/or attenuation of fibrosis diseases, in particular excessive scars such as keloids or hypertrophic scars.

The present invention relates also to a method of treating and/or preventing and/or attenuating fibrosis diseases, in particular excessive scars such as keloids or hypertrophic scars, comprising the administration to a person in need thereof of an effective amount of said pharmaceutical composition.

The pharmaceutical compositions of the invention are more particularly intended to topical (e.g. transdermal) administration or parenteral (e.g. subcutaneous) administration, preferably topical administration.

For the purpose of the invention, the term "pharmaceutically acceptable" is intended to mean what is useful to the preparation of a pharmaceutical composition, and what is generally safe and non toxic, for a pharmaceutical use.

By "pharmaceutical composition" is meant in the framework of the present invention a composition having preventive and curative properties towards diseases, and more particularly fibrosis diseases as defined above. In the framework of the present invention, it can be a cosmeceutical (i.e. a composition having both cosmetic and pharmaceutical properties) or dermatological composition.

By "topical" administration is meant in the framework of the present invention an administration on the skin or on mucous membranes (e.g. conjunctiva).

The compounds of the invention can be used in a pharmaceutical composition at a dose ranging from 0.01 mg to 1000 mg a day, administered in only one dose once a day or in several doses along the day, for example twice a day in equal doses. The daily administered dose is advantageously comprises between 5 mg and 500 mg, and more advantageously between 10 mg and 200 mg. However, it can be necessary to use doses out of these ranges, which could be noticed by the person skilled in the art.

For parenteral, in particular subcutaneous, administration, the pharmaceutical composition according to the invention can be in the form of an aqueous suspension or solution which is advantageously sterile.

Such parenteral (e.g. subcutaneous) compositions will contain advantageously a physiologically acceptable medium, generally based on an isotonic saline solution, i.e. 0.9% NaCl aqueous solution (normal saline). Non-aqueous water miscible co-solvent, such as ethanol, glycerin, propylene glycol or n-lactamide, can also be used.

The parenteral composition of the invention can also comprise one or more additive(s), such as suspending agents, wetting agents, preservatives, antioxidants, chelating agents, buffering agents, tonicity adjusting agents, etc. Such additives are conventional to those of skill in the art.

Suspending agents can be an alginate, sodium carboxymethyl cellulose, methyl cellulose, hydroxyl methyl cellulose, hydroxyl ethyl cellulose, hydroxylpropyl methyl cellulose, microcrystalline cellulose, a gum such as acacia, tragacanth or xanthan gum, gelatin, a carrageenan, polyvinyl pyrrolidone, etc.

Wetting agents can be glycerin, propylene glycol or also nonionic surfactants such as a lecithin, a polysorbate or a poloxamer.

Preservatives can be benzyl alcohol, phenol, cresol, chlorobutanol, a paraben such as methylparaben, propylparaben or propylparaben, benzalkonium chloride, benzethonium chloride, etc.

Antioxidants can be ascorbic acid, citric acid, acetylcysteine, sulfurous acid salts (bisulfite, metabisulfite), monothioglycerol, sodium formaldehyde sulfoxylate, thiourea, tocopherol, etc.

Chelating agents can be an ethylene diamine tetraacetic acid (EDTA) salt.

Buffering agents can be acetate, citrate, tartrate, phosphate, triethanolamine (TRIS), etc.

Tonicity adjusting agents can be dextrose, glycerol, sodium chloride, glycerin, mannitol, etc.

For topical administration, the pharmaceutical composition according to the invention can be in the usual forms for a topical administration including creams, lotions, serums, gels, foams, dispersions, suspensions, emulsions, sprays, shampoos, masks, body milks, etc. The active ingredient can be administered in unit forms for administration, mixed with conventional pharmaceutical carriers, to animals, preferably mammals including humans.

Such topical compositions generally contain a physiologically acceptable medium, notably based on water or a solvent such as alcohols (for ex. ethanol), ethers or glycols.

The topical composition of the invention can also comprise one or more additive(s), such as antioxidants, emollients, humectants, thickening agents, fragrances, preservatives, pigments or colorants, or opacifiers. Such additives are conventional to those of skill in the art.

Antioxidants can be used to protect ingredients of the composition from oxidizing agents that are included within or come in contact with the composition. Examples of antioxidants include ascorbyl palmitate, butylated hydroxyanisole, butylated hydroxytoluene, potassium propyl gallate, octyl gallate, dodecyl gallate, phenyl-α-napthyl-amine, and tocopherols such as α-tocopherol.

Emollients are agents that soften and smooth the skin. Examples of emollients include oils and waxes such as siloxanes such as dimethicone and derivatives thereof, microcrystaline wax, polyethylene, triglyceride esters such as those of castor oil, cocoa butter, safflower oil, corn oil, olive oil, cod liver oil, almond oil, palm oil, squalene, and soybean oil, acetylated monoglycerides, ethoxylated glycerides, fatty acids, alkyl esters of fatty acids, alkenyl esters of fatty acids, fatty alcohols, fatty alcohol ethers, ether-esters, lanolin and derivatives of lanolin, polyhydric alcohol esters, wax esters such as beeswax, vegetable waxes, phospholids, sterols, isopropyl palmitate or glyceryl stearate.

Humectants are used to increase and maintain moisture in the skin. Examples of humectants include propylene glycol, butylene glycol, polyethylene glycol (PEG) (such as PEG-4 to PEG-32), glycerol (also called glycerin), sorbitol, xylitol, maltitol, mannitol, polydextrose, hyaluronic acid and its salts (such as sodium or potassium salt), urea, aloe vera, honey, etc.

Thickening agents are used to increase the viscosity and thickness of the composition. Examples of thickening agents include lipid thickening agents such as Cetyl Alcohol, Stearyl Alcohol, Myristyl Alcohol, Carnauba Wax, or Stearic acid; naturally derived thickening agents such as Cellulose derivatives like Hydroxyethylcellulose, Guar gum, Locust Bean Gum, Xanthan Gum, or Gelatin; mineral thickening agents such as Silica, Bentonite, or Magnesium Aluminum Silicate; synthetic thickening agents such as Carbomer; ionic thickening agents such as NaCl.

Examples of fragrances or perfume include peppermint, rose oil, rose water, aloe vera, clove oil, menthol, camphor, eucalyptus oil, and other plant extracts. To eliminate certain odours from compositions, masking agents may be used.

Preservatives can be used to protect the composition from degradation. Examples of preservatives include phenoxyethanol, butylparaben, ethylparaben, methylparaben, propylparaben, benzalkonium chloride, benzethonium chloride, benzoic acid, benzyl alcohol, and mixtures thereof such as liquipar oil. However, the composition of the present invention can be preservative free.

Pigments or colorants are used to modify the color of the composition, such as to obtain a white composition.

Opacifiers, such as titanium oxide, are used in clear or transparent composition in order to render it opaque. The present invention can thus be clear or opaque according to the use or not of an opacifier.

The pharmaceutical composition according to the invention can be used in combination with, and more particular after, a laser or surgical treatment. Indeed, a patient suffering from a fibrosis disease, in particular excessive scars such as keloids or hypertrophic scars, can be first treated with laser or by surgery to eliminate the excess fibrous connective tissue and then a pharmaceutical composition according to the invention can be applied topically on the wound during its healing in order to prevent the reappearance of the excess fibrous connective tissue.

The present invention concerns also a dressing comprising a pad, compress or sponge impregnated with a pharmaceutical composition according to the present invention as defined above comprising at least one compound of formula I as defined previously, according to any of the disclosed embodiments, or a salt thereof, a solvate, a tautomer, a stereoisomer or a mixture of stereoisomers in any proportions, in particular a mixture of enantiomers, and particularly a racemate mixture, and at least one pharmaceutically acceptable excipient.

Such a dressing can be applied to an injury/a wound during the healing step in order to prevent or reduce the appearance of keloids or hypertrophic scars. Thus it can be for use in the treatment and/or prevention and/or attenuation, notably in the prevention, of fibrosis diseases, in particular excessive scars such as keloids or hypertrophic scars.

It is thus preferably sterile.

Such a dressing can be more particularly a pressure dressing.

The pad, compress or sponge can be made of various materials, preferably absorbent materials, such as cotton, gauze, a porous polymer material, or a combination thereof, notably cotton and/or gauze.

It can also comprise a bandage or adhesive means in order to maintain the pad or compress in close contact with the injury or wound.

The present invention relates also to a dressing as defined above for use in the treatment and/or prevention and/or attenuation of fibrosis diseases, in particular excessive scars such as keloids or hypertrophic scars.

The present invention relates also to the use of a dressing as defined above for the manufacture of a medicament intended for the treatment and/or prevention and/or attenuation of fibrosis diseases, in particular excessive scars such as keloids or hypertrophic scars.

The present invention relates also to the use of as defined above in the treatment and/or prevention and/or attenuation of fibrosis diseases, in particular excessive scars such as keloids or hypertrophic scars.

The present invention relates also to a method of treating and/or preventing and/or attenuating fibrosis diseases, in particular excessive scars such as keloids or hypertrophic scars, comprising the application to a person in need thereof of a dressing as defined above.

This dressing can be used in combination with, and more particular after, a laser or surgical treatment. Indeed, a patient suffering from a fibrosis disease, in particular excessive scars such as keloids or hypertrophic scars, can be first treated with laser or by surgery to eliminate the excess fibrous connective tissue and then a dressing according to the invention can be applied on the wound during its healing in order to prevent the reappearance of the excess fibrous connective tissue.

The present invention is illustrated by the following non-limitative examples.

EXAMPLES

The following abbreviations have been used in the examples:
ACTA2: Actin, alpha2, smooth muscle, aorta
BCA: Bicinchoninic acid
COL1A: Collagen, type I, alpha 1
COL3A1: Collagen, type III, alpha 1
COL5A1: Collagen, type V, alpha 1
COL8A1: Collagen, type VIII, alpha 1
DCN: Decorin
DMEM: Dulbecco's modified Eagle's medium
DPT: Dermatopontin
ECM: Extracellular matrix
ELN: Elastin
FBLN5: Fibulin 5
FCS: Fetal calf serum
KF: Keloid fibroblasts
LEPR: Leptin receptor
MMP: Matrix metalloproteinase
MMP1: Matrix metallopeptidase 1 (interstitial collagenase)
MMP3: Matrix metallopeptidase 3 (stromelysin, progelatinase)
mRNA: Messenger ribonucleic acid
NF: Normal fibroblasts
PBS: Phosphate buffered saline
PCOLCE: Procollagen C-endopeptidase enhancer
PCR: Polymerase Chain Reaction
RT-qPCR: Reverse Transcription quantitative PCR
sem: standard error of the mean
TGF-β: Transforming growth factor beta
TFPI2: Tissue factor pathway inhibitor 2
TMB: 3,3',5,5'-Tetramethylbenzidine
TP53: Tumor protein p53

Compounds 1, 2, 3 and 4 used in the examples below were prepared as described in WO2015/140178.

During excessive scar formation, a dysfunction of the healing process is observed, leading to an excessive matrix synthesis and/or deficient matrix degradation and remodeling.

In the present invention, the effect of $CF_2$ glycopeptide of formula I was evaluated on the expression of a panel of genes that are involved in mechanism of reducing excessive scars. The study was performed on normal and aged human fibroblasts at mRNA levels. An additional study was performed on normal and keloid fibroblasts at protein levels. In normal human dermal fibroblasts, compound 1 can inhibit the expression of genes implicated in extracellular matrix (ECM) synthesis (COL1A1, COL3A1, ELN, COL5A1, COL8A1, DCN, DPT, FBLN5, PCOLCE) and can stimulate the expression of genes implicated in ECM degradation (MMP1, MMP3 and TFPI2). The results are presented in Table 1.

Besides keloid scars are characterized by a collection of atypical fibroblasts with excessive deposition of extracellular matrix components. An overproduction and accumulation of collagen (increased type I/III collagen ratio) and elastin, as well as a low level of matrix metalloproteinases MMP1 and MMP3 have been mainly observed in keloids (*Histol. Histopathol.* 2015, 30, 1033-1057).

That is why the expression of genes implicated in extra-cellular matrix generation, as collagen 1, collagen 3 and elastin, and in extracellular matrix degradation, as MMP1, was particularly studied in fibroblasts cultures.

Compounds 1, 2, 3 and 4 can modulate gene profile in a way to avoid the ECM product deposit by decreasing the expression of COL1A1, COL3A1 and ELN; and also by increasing the expression of MMP1 in aged human dermal fibroblasts. The results are presented in Table 2.

In addition, it has been showed that expression of transforming growth factor TGF-β impact the formation of keloids. The expression of TGF-β receptors TGF-βR1 and TGF-βR2 are higher in keloid fibroblasts compared to normal human dermal fibroblasts (*Plast. Reconstr. Surg.* 2001, 108, 423-429). Besides, leptin also play a major role in wound healing process and it has been shown that leptin is overexpressed in keloids and hypertrophic scars (*Appl. Immunohistochem. Mol. Morphol.* 2016, 24, 296-306). Thus, LEPR and TGFβR2 mRNA expression was measured in normal fibroblasts. The expression of these genes involved in cell proliferation was reduced in the presence of compound 1. The results are presented in Table 3.

Then, compound 1 also decreases the expression of the ACTA2 gene encoding the alpha smooth muscle actin which has been described to increase in fibrosis/hypertrophic scar or keloid. The results are presented in Table 4.

Finally, to support the results obtained at mRNA levels, an evaluation of compound 1 on the production of proteins, particularly on collagen I and collagen III, in culture of human normal fibroblasts (NF) and keloid fibroblasts (KF) has been performed.

In accordance with what is described in the literature an increased collagen I/collagen III ratio was observed in keloids fibroblasts compared to normal fibroblasts control.

The results show that, in the presence of compound 1, the collagen I/collagen III ratio in KF decreased up to a value close to NF control. Compound 1 inhibits the synthesis of collagens I and III in fibroblasts obtained from keloid scars. The results are presented in Table 5.

In conclusion, results obtained at mRNA and proteins levels indicate that compounds of formula I can treat and/or prevent and/or attenuate fibrosis diseases, in particular hypertrophic scars and keloids.

General Experimental Procedure

1. Effects of Compounds 1, 2, 3, 4 on Expression of Genes Involved in ECM Synthesis or Degradation, in Normal or Aged Fibroblast Culture (Analysis of mRNA Expression Profile by RT-qPCR)

In the present study, the transcriptional effects (modulation of gene expression) of compounds 1, 2, 3, 4 was evaluated on "aged" human dermal fibroblasts (Hayflick model) and normal human dermal fibroblasts (NHDF) in order to assess their potential effect.

More specifically, the effects of the compound on "aged" fibroblasts and NHDF were evaluated using RT-qPCR technology. Extracted mRNAs were analyzed using a PCR for the analysis of target genes (including housekeeping genes) selected for their importance in dermal fibroblast physiology.

Materials and Methods a) Biological Model

Subculturing: Human dermal fibroblasts were grown in culture medium composed of DMEM supplemented with L-glutamine (2 mM), Penicillin (50 U/ml), Streptomycin (50 µg/ml) and Fetal calf serum (FCS) 10% in 37° C. and 5% $CO_2$ incubator.

Assay: Cells were used at the 7th passage (normal fibroblasts) or the 17th passage (aged fibroblasts). The assay medium was composed of DMEM supplemented with L-glutamine (2 mM), Penicillin (50 U/ml), Streptomycin (50) µg/ml and FCS 1%.

b) Test Compounds

An intermediate solution of compounds 1, 2, 3, 4 was prepared in assay medium at concentration 100 mg/ml (pH=7.4) to be tested at 94 mM or 34 mM in normal or aged fibroblasts culture.

c) Cultures and Treatments

Aged or normal fibroblasts were seeded in 12-well or 24-well plates and cultured for 24 to 48 hours in culture medium. The medium was then removed and replaced by assay medium containing the test compound (treated) or not (control) and the cells were incubated for 24 hours. All experimental conditions were performed in n=3. At the end of incubation, the cells were washed in a phosphate buffered saline (PBS) solution and immediately frozen at −80° C.

d) Differential Gene Expression Analysis by RT-qPCR Method

The expression of markers was analyzed using RT-qPCR method on mRNA extracted from the cell monolayers of each experimental condition (before RNA extraction, the replicates of the same experimental condition were pooled). The analysis of transcripts was performed in n=2 using a PCR array.

Reverse Transcription:

Total RNA was extracted from each sample using TriPure Isolation Reagent® or NucleoSpin® RNA Plus kit (Macherey-Nagel) according to the supplier's instructions. The amount and quality of RNA were evaluated using electrophoresis (Bioanalyzer 2100, Agilent technologies). Potential contaminant traces of genomic DNA were removed using the DNAfree system (Ambion). The complementary DNA (cDNA) was synthetized by reverse transcription of total RNA in presence of oligo(dT) and "Transcriptor Reverse Transcriptase" (Roche). Quantification of cDNA was performed using a spectrophotometer (Nanovue, GE Healthcare) and cDNA quantities were adjusted.

Quantitative PCR:

The PCRs (Polymerase Chain Reactions) were performed using the "LightCycler®" system (Roche Molecular System Inc.) according to the supplier's instructions. The reaction mix (10 µl final) was prepared as follows: 2.5 µl of cDNA, primers (forward and reverse), reagent mix containing taq DNA polymerase, SYBR Green I and $MgCl_2$.

Data Management of Quantitative PCR:

Raw data were analyzed using Microsoft Excel® software. The incorporation of fluorescence in amplified DNA was continuously measured during the PCR cycles. This resulted in a "fluorescence intensity" versus "PCR cycle" plot allowing the evaluation of a relative expression (RE) value for each marker.

The value selected for RE calculations is the "output point" (Ct) of the fluorescence curve. For a considered marker, the highest is the cycle number, the lowest is the mRNA quantity.

The RE value was calculated with the formula: $(\frac{1}{2}^{number\ of\ cycles}) \times 10^6$.

Two housekeeping genes RPS28 and GAPDH were used for data normalization since their expression is constitutive and theoretically stable. The mean relative expression of housekeeping genes was calculated for all test conditions. The level of expression of the target markers was compared to the mean expression level of these 2 markers for all test conditions (% control mean HK).

Classification of Effects ("Treated" Conditions Versus "Normal Control" or "Aged Control"):

For a standardized interpretation, the following table was used:

| Relative expression (% of control) | Classification of effects |
|---|---|
| >300% | Strong stimulation |
| >200% and ≤300% | Stimulation |
| ≥30% and <50% | Inhibition |
| <30% | Strong inhibition |

II. Evaluation of the Effects of Compound 1 on Collagen Expression in Human Keloid Fibroblasts Culture Materials and Methods a) Biological Model Primary cultures of keloid fibroblasts (KF) and normal fibroblasts (NF) were obtained from operative wastes (keloid and abdominoplasty). After thawing, cells were grown in Dulbecco's modified Eagle's medium (DMEM) supplemented with 10% of fetal calf serum, 40 mg/l of gentamicin and 2 mg/l of fungizone (DMEMc), in an incubator at 37° C., 5% $CO_2$. Culture medium was changed twice a week and cells were subcultured by trypsinization when confluence was reached. Cells were used under 10 passages.

b) Tested Compound

Compound 1 was directly diluted in culture medium at 5 mg/ml.

c) Cell Culture and Collect

Fibroblasts were seeded in 6 wells culture plate at the concentration of $0.08 \cdot 10^6$ cells/well (n=6). After 48 hours of culture, wells were washed with 3 ml of PBS. 2 ml of each solution of tested compound were added per wells. Plates were then incubated at 37° C. with 5% $CO_2$. After 48 hours of culture, 4×200 µl of supernatant were collected in Eppendorf vials containing 20 µl of protease inhibitor cocktail and stored at −80° C. until collagen synthesis analysis. The monolayer cells were then washed with 3 ml of PBS and 250 µl of 0.1N NaOH were added. After 10 minutes supernatants were removed into an Eppendorf and stored at −20° C. until proteins analysis.

d) Evaluation of Collagen Synthesis

The synthetized collagen quantity is expressed as the ratio of quantity of collagen vs quantity of total proteins in the sample.

Evaluation of the Quantity of Total Proteins in the Sample:

The quantity of total protein was determined using a biochemical test, the bicinchoninic acid assay (BCA assay). The total protein concentration is exhibited by a color change of the sample solution from green to purple in proportion to protein concentration, which can then be measured using colorimetric techniques. Bicinchoninic acid (BCA) as soluble sodium salt in aqueous medium reacts in a stably, sensitive and highly specific manner with cuprous ions. Proteins react with cupric ions (issued from copper(II) sulfate) in an alkaline medium to produce cuprous ions. Then, two molecules of BCA with one cuprous ion react to form a purple complex which shows an absorption peak at 562 nm. A standard curve (0-2 mg/ml) is established with a bovine serum albumin solution. 20 µl of each tested concentration of the standard or of the sample are placed in wells of a 96 well-plate, in duplicate. 200 µl of Pierce reagent (comprising BCA and copper(II) sulfate) were added and the plate is incubated for 30 minutes at 37° C. Absorbance is read immediately at 550 nm (Spectrophotometer Multiscan Ex, Thermo). The standard curve is drawn and the sample protein concentration is determined with this curve. The results are expressed in mg protein/ml.

Evaluation of Collagen I Synthesis:

Collagen I synthesis was evaluated by Enzyme-linked immunosorbent assay with an ELISA kit (USCN SEA571Hu, Euromedex). The assay was performed according to the supplier's instructions. To summarize, the microtiter plate provided in the kit is pre-coated with an antibody specific to collagen I. Standard or samples are added to the wells with a biotin-conjugated antibody specific to collagen I. Next, avidin conjugated to Horseradish Peroxidase (HRP) is added to each microplate well and incubated. After TMB substrate solution is added, only those wells that contain collagen I, biotin-conjugated antibody and enzyme-conjugated avidin will exhibit a change in color. The enzyme-substrate reaction is terminated by the addition of sulfuric acid solution and the color change is measured spectrophotometrically at 450 nm. The concentration of collagen I in the samples is then determined by comparing the optical density of the samples to the standard curve. The results were expressed as pg of collagen I by mg of proteins.

Evaluation of Collagen III Synthesis:

Collagen III synthesis is performed by Enzyme-linked immunosorbent assay with an ELISA kit (USCN SEA576Hu, Euromedex). The assay was performed according to the supplier's instructions. To summarize, the microtiter plate provided in the kit is pre-coated with an antibody specific to collagen III. Standard or samples are then added to the wells with a biotin-conjugated antibody specific to collagen III. Next, avidin conjugated to Horseradish Peroxidase (HRP) is added to each microplate well and incubated. After TMB substrate solution is added, only those wells that contain collagen III, biotin-conjugated antibody and enzyme-conjugated avidin will exhibit a change in color. The enzyme-substrate reaction is terminated by the addition of sulfuric acid solution and the color change is measured spectrophotometrically at 450 nm. The concentration of collagen III in the samples is then determined by comparing the optical density of the samples to the standard curve. The results were expressed as ng of collagen III by mg of proteins.

Statistical Analysis:

Data are expressed as mean+/−sem. A variance analysis with one factor was performed for cytotoxicity study followed if necessary by a Fisher test. A variance analysis with two factors was performed for synthesis study followed if necessary by a Fisher test. A p value less than 0.05 is considered significant.

Data Management:

To be able to compare the results, the collagen quantity is expressed as the ratio of quantity of collagen vs quantity of total proteins in the sample.

TABLE 1

Effect of compound 1 (at 94 mM) on gene expression involved in ECM synthesis and degradation in normal human dermal fibroblasts.

| | | Normal fibroblasts | | |
| --- | --- | --- | --- | --- |
| | | | Compound 1 | |
| | Genes | Control Cycles | Cycles | % Control Mean HK |
| ECM synthesis/ ECM assembly | COL1A1 | 14.25 | 17.03 | 17 |
| | | 14.35 | 17.13 | |
| | COL3A1 | 20.14 | 22.87 | 18 |
| | | 20.06 | 22.72 | |
| | COL5A1 | 20.58 | 22.87 | 24 |
| | | 20.67 | 22.87 | |
| | COL8A1 | 22.1 | 24.57 | 22 |
| | | 22.14 | 24.51 | |
| | DCN | 17.89 | 19.94 | 29 |
| | | 17.91 | 19.89 | |
| | DPT | 21.86 | 24.18 | 24 |
| | | 21.95 | 24.14 | |
| | ELN | 25.47 | 27.17 | 34 |
| | | 25.35 | 27.16 | |
| | FBLN5 | 23.11 | 24.21 | 48 |
| | | 22.65 | 24.06 | |
| | PCOLCE | 20.75 | 22.02 | 49 |
| | | 20.84 | 22.04 | |
| ECM degradation | MMP1 | 20.87 | 16.24 | 2759 |
| | | 20.77 | 16.24 | |
| | MMP3 | 22.9 | 20.88 | 448 |
| | | 22.86 | 20.97 | |
| | TFPI2 | 29.91 | 26.14 | 1694 |
| | | 29.99 | 26.01 | |

Up-regulated genes (arbitrary selection for stimulation): % > 200

Down-regulated genes (arbitrary selection for inhibition): % < 50

TABLE 2

Effect of compounds 1, 2, 3 and 4 (at 34 mM) on gene expression involved in ECM synthesis and degradation in "aged" human dermal fibroblasts.

| | | | Compound 1 | | Compound 2 | | Compound 3 | | Compound 4 | |
|---|---|---|---|---|---|---|---|---|---|---|
| | Genes | Control Cycles | Cycles | % Control Mean HK | Cycles | % Control Mean HK | Cycles | % Control Mean HK | Cycles | % Control Mean HK |
| ECM synthesis/ ECM assembly | COL1A1 | 14.45 14.51 | 16.23 16.16 | 31 | 16.60 16.70 | 23 | 16.29 16.01 | 33 | 15.67 15.73 | 42 |
| | COL3A1 | 21.63 21.65 | 22.94 23.09 | 39 | 23.29 23.44 | 32 | 23.46 23.21 | 33 | 23.84 23.85 | 21 |
| | ELN | 27.83 27.52 | 29.89 30.08 | 21 | 29.97 30.21 | 20 | 28.99 29.28 | 39 | 29.72 30.04 | 21 |
| ECM degradation | MMP1 | 20.82 20.78 | 17.53 17.60 | 962 | 17.14 17.13 | 1341 | 18.93 18.81 | 405 | 18.33 18.35 | 535 |

Up-regulated genes (arbitrary selection for stimulation): % > 200
Down-regulated genes (arbitrary selection for inhibition): % < 50

TABLE 3

Effect of compound 1 (at 94 mM) on gene expression involved in cell proliferation in normal human dermal fibroblasts.

| | | Normal fibroblasts | | |
|---|---|---|---|---|
| | | | Compound 1 | |
| | Genes | Control Cycles | Cycles | % Control Mean HK |
| Cell proliferation | LEPR | 27.60 28.01 | 29.64 29.16 | 38 |
| | TGFBR2 | 25.21 25.24 | 27.51 27.26 | 26 |

Up-regulated genes (arbitrary selection for stimulation): % > 200
Down-regulated genes (arbitrary selection for inhibition): % < 50

TABLE 4

Effect of compound 1 (at 94 mM) on gene expression involved in cytoskeletal integrity in normal human dermal fibroblasts.

| | | Normal fibroblasts | | |
|---|---|---|---|---|
| | | | Compound 1 | |
| | Genes | Control Cycles | Cycles | % Control Mean HK |
| Cytoskeletal integrity | ACTA2 | 24.68 24.83 | 26.76 26.87 | 28 |

Up-regulated genes (arbitrary selection for stimulation): % > 200
Down-regulated genes (arbitrary selection for inhibition): % < 50

TABLE 5

Synthesis of Collagen I and Collagen III proteins in the presence or not of compound 1 (at 9.4 mM) in normal and keloids fibroblasts.

| | | Normal fibroblasts | | | | Keloids fibroblasts | | | |
|---|---|---|---|---|---|---|---|---|---|
| | | NF Control | | NF + compound 1 | | KF Control | | KF + compound 1 | |
| | | Mean | sem | Mean | sem | Mean | sem | Mean | sem |
| Protein | Collagen I (pg/mg) | 103.5 | 5.61 | 28.85*** | 5.04 | 149.89*** | 12.58 | 44.68### | 6.03 |
| Protein | Collagen III (ng/mg) | 11.84 | 0.82 | 6.57*** | 0.61 | 6.46*** | 0.46 | 4.42# | 0.25 |
| Ratio | Collagen I / Collagen III | $8.74 \cdot 10^{-3}$ | | $4.39 \cdot 10^{-3}$ | | $23.20 \cdot 10^{-3}$ | | $10.11 \cdot 10^{-3}$ | |

***$p < 0.001$ versus NF Control
$p < 0.05$ versus KF Control
$p < 0.001$ versus KF Control

The invention claimed is:

1. A method of treating and/or preventing and/or attenuating a fibrosis disease, comprising the administration to a person in need thereof of an effective amount of a compound of following formula (I):

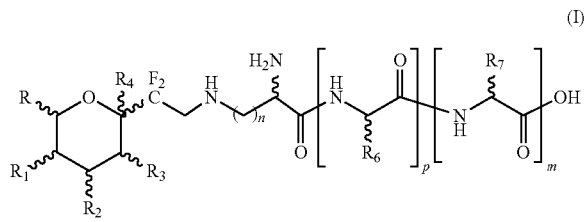
(I)

or a salt thereof, a solvate, a tautomer, a stereoisomer or a mixture of stereoisomers in any proportions,
in which:
n represents an integer from 1 to 6,
m represents 0 or 1,
p represents 0 or 1
R represents H, F, $CH_3$, $CH_2F$, or $CH_2OH$,
$R_1$, $R_2$ and $R_3$ represent, independently from one another, H, F, or OH,
$R_4$ represents a hydrogen, a halogen, or OH, and
$R_6$ and $R_7$ represent, independently from each other, a hydrogen, a ($C_1$-$C_6$)alkyl, an aryl, or an aryl-($C_1$-$C_6$)alkyl.

2. The method according to claim 1, wherein the fibrosis disease is excessive scars.

3. The method according to claim 2, wherein the excessive scars are keloids or hypertrophic scars.

4. The method according to claim 1, wherein the compound of formula (I) has one of the following formulas (Ia), (Ib), (Ic):

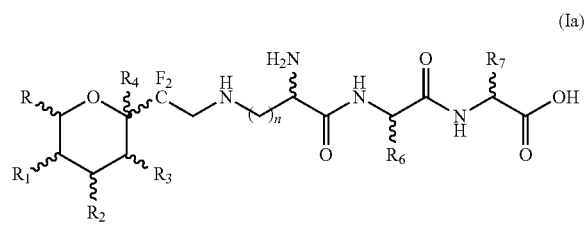
(Ia)

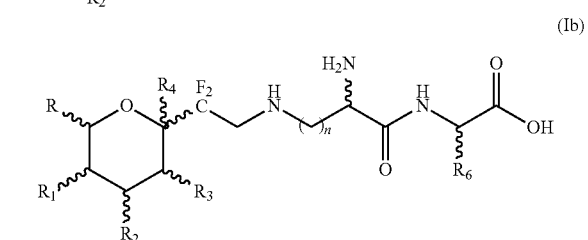
(Ib)

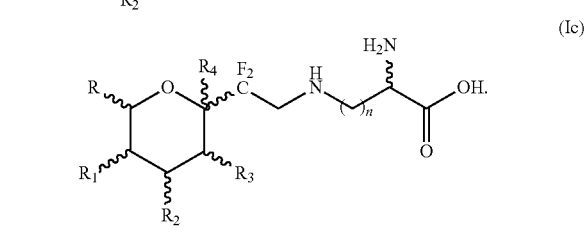
(Ic)

5. The method according to claim 1, wherein n represents an integer from 2 to 6.

6. The method according to claim 1, wherein R represents a $CH_2OH$ group.

7. The method according to claim 1, wherein $R_1$, $R_2$ and $R_3$ each represent a OH group.

8. The method according to claim 1, wherein $R_4$ represents a OH group.

9. The method according to claim 1, wherein $R_6$ and $R_7$ represent, independently from each other, a ($C_1$-$C_6$)alkyl, an aryl or an aryl-($C_1$-$C_6$)alkyl.

10. The method according to claim 1, wherein the compound of formula (I) is chosen among the following compounds:

Compound 1
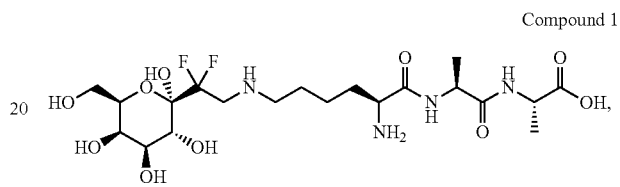

Compound 2
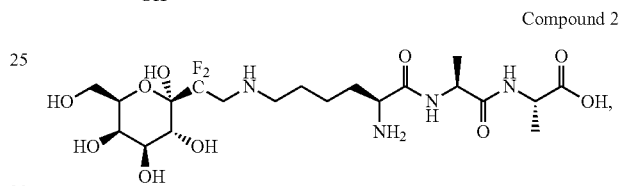

Compound 3
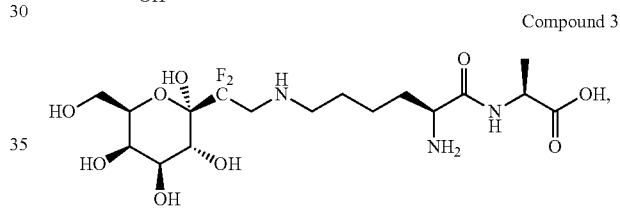

Compound 4
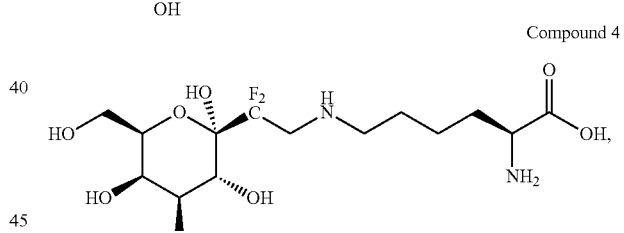

and the salts and/or solvates thereof.

11. A method of treating and/or preventing and/or attenuating a fibrosis disease, comprising the administration to a person in need thereof of an effective amount of a pharmaceutical composition comprising at least one pharmaceutically acceptable excipient and at least one compound of following formula (I):

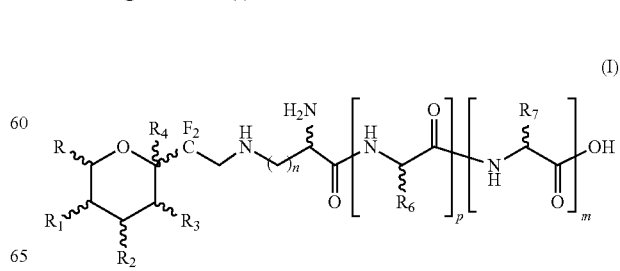
(I)

or a salt thereof, a solvate, a tautomer, a stereoisomer or a mixture of stereoisomers in any proportions,
in which:
n represents an integer from 1 to 6,
m represents 0 or 1,
p represents 0 or 1
R represents H, F, $CH_3$, $CH_2F$, or $CH_2OH$,
$R_1$, $R_2$ and $R_3$ represent, independently from one another, H, F, or OH,
$R_4$ represents a hydrogen, a halogen, or OH, and
$R_6$ and $R_7$ represent, independently from each other, a hydrogen, a ($C_1$-$C_6$)alkyl, an aryl, or an aryl-($C_1$-$C_6$) alkyl.

12. The method according to claim 11, wherein the fibrosis disease is excessive scars.

13. The method according to claim 12, wherein the excessive scars are keloids or hypertrophic scars.

14. The method according to claim 11, wherein n represents an integer from 2 to 6; R represents a $CH_2OH$ group; $R_1$, $R_2$ and $R_3$ each represent a OH group; $R_4$ represents a OH group; and $R_6$ and $R_7$ represent, independently from each other, a ($C_1$-$C_6$)alkyl, an aryl or an aryl-($C_1$-$C_6$)alkyl.

15. The method according to claim 11, wherein the compound of formula (I) is chosen among the following compounds:

Compound 1

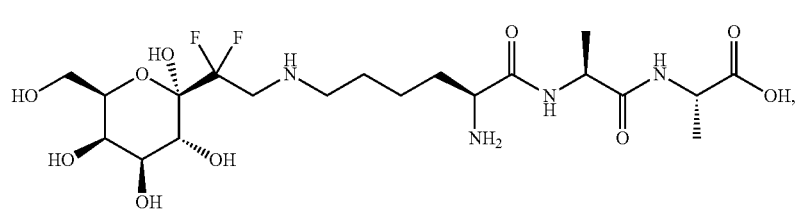

Compound 2

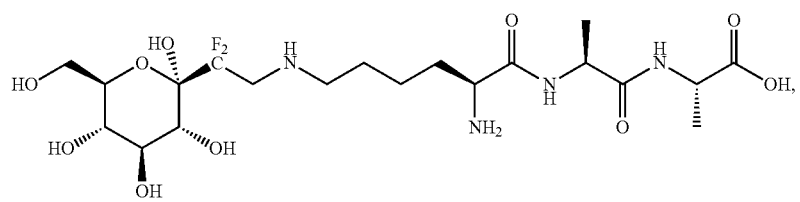

Compound 3

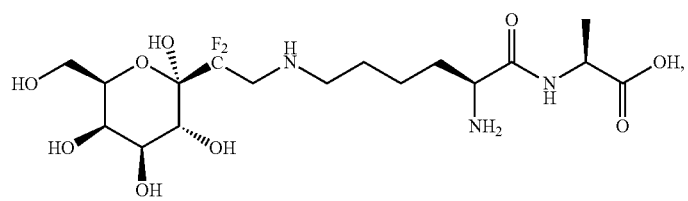

Compound 4

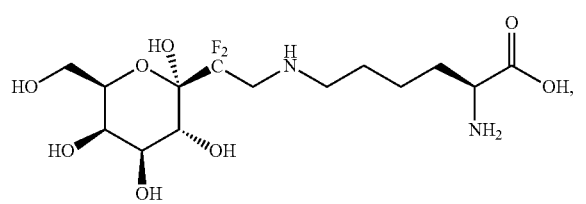

and the salts and/or solvates thereof.

16. The method according to claim 11, wherein the pharmaceutical composition is administered topically in combination with or after a laser or surgical treatment.

17. A dressing comprising a pad, compress or sponge impregnated with a pharmaceutical composition comprising at least one pharmaceutically acceptable excipient and at least one compound of following formula (I):

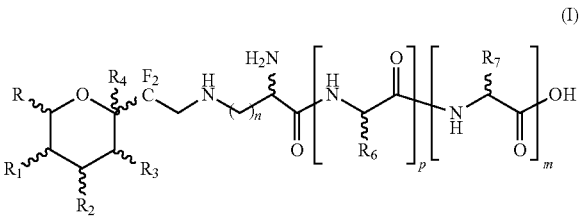

(I)

or a salt thereof, a solvate, a tautomer, a stereoisomer or a mixture of stereoisomers in any proportions,
in which:
n represents an integer from 1 to 6,
m represents 0 or 1,
p represents 0 or 1
R represents H, F, $CH_3$, $CH_2F$, or $CH_2OH$,
$R_1$, $R_2$ and $R_3$ represent, independently from one another, H, F, or OH,
$R_4$ represents a hydrogen, a halogen, or OH, and
$R_6$ and $R_7$ represent, independently from each other, a hydrogen, a ($C_1$-$C_6$)alkyl, an aryl, or an aryl-($C_1$-$C_6$) alkyl.

18. The dressing according to claim 17, wherein n represents an integer from 2 to 6; R represents a $CH_2OH$ group; $R_1$, $R_2$ and $R_3$ each represent a OH group; $R_4$ represents a OH group; and $R_6$ and $R_7$ represent, independently from each other, a $(C_1-C_6)$alkyl, an aryl or an aryl-$(C_1-C_6)$alkyl.

19. The dressing according to claim 17, wherein the compound of formula (I) is chosen among the following compounds:

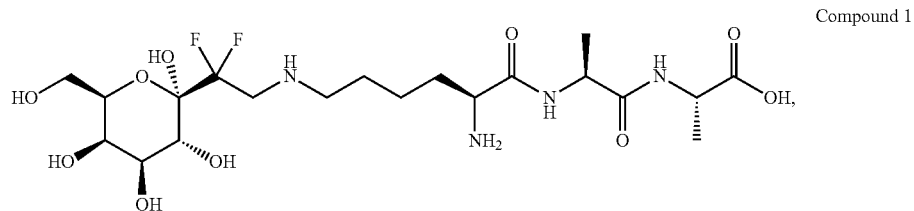

Compound 1

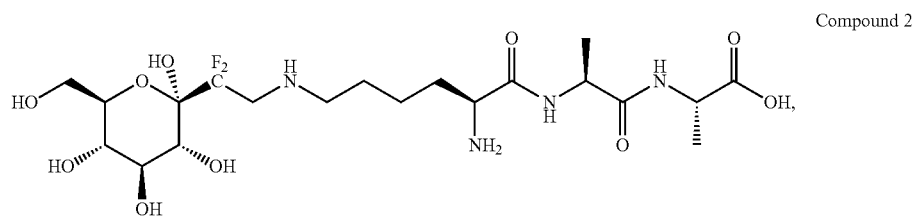

Compound 2

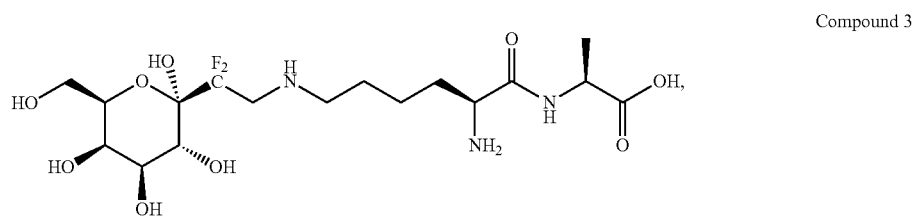

Compound 3

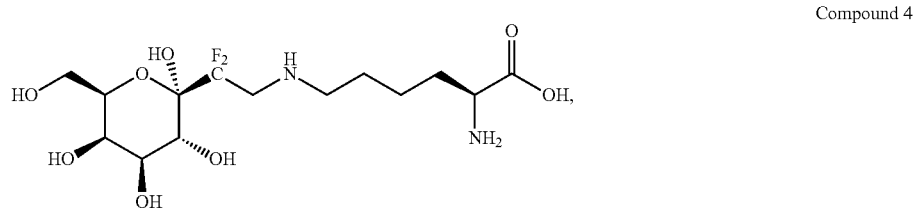

Compound 4 and the salts and/or solvates thereof.

20. A method of treating and/or preventing and/or attenuating a fibrosis disease, comprising the application to a person in need thereof of a dressing according to claim 17.

21. The method according to claim 20, wherein the dressing is applied in combination with or after a laser or surgical treatment.

\* \* \* \* \*